United States Patent
Suzuki et al.

(10) Patent No.: US 9,057,703 B2
(45) Date of Patent: Jun. 16, 2015

(54) PARTICLE DETECTION DEVICE

(75) Inventors: Akihiro Suzuki, Osaka (JP); Hideaki Fujita, Osaka (JP); Seiichi Nagatome, Osaka (JP); Kazushi Fujioka, Osaka (JP); Hiroki Okuno, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 14/239,892

(22) PCT Filed: Jun. 15, 2012

(86) PCT No.: PCT/JP2012/065349
§ 371 (c)(1),
(2), (4) Date: Feb. 20, 2014

(87) PCT Pub. No.: WO2013/035405
PCT Pub. Date: Mar. 14, 2013

(65) Prior Publication Data
US 2014/0175304 A1    Jun. 26, 2014

(30) Foreign Application Priority Data
Sep. 9, 2011  (JP) .................. 2011-197392

(51) Int. Cl.
*G01N 21/64*    (2006.01)
*G01N 15/06*    (2006.01)
*G01N 15/00*    (2006.01)

(52) U.S. Cl.
CPC .... *G01N 21/6486* (2013.01); *G01N 2015/0065* (2013.01); *G01N 2015/0046* (2013.01); *G01N 15/0612* (2013.01); *G01N 15/0656* (2013.01)

(58) Field of Classification Search
CPC ............... G01N 15/0656; G01N 2015/0065; G01N 2015/0046; G01N 21/6468
USPC ........................................ 250/459
See application file for complete search history.

(56) References Cited

U.S. PATENT DOCUMENTS

| | | | |
|---|---|---|---|
| 2005/0247868 | A1 | 11/2005 | Call et al. |
| 2006/0257853 | A1 | 11/2006 | Herman |
| 2008/0078256 | A1 | 4/2008 | Christie et al. |

(Continued)

FOREIGN PATENT DOCUMENTS

| | | |
|---|---|---|
| EP | 0 289 789 A1 | 11/1988 |
| JP | 58-39586 U | 3/1983 |

(Continued)

OTHER PUBLICATIONS

Official Communication issued in International Patent Application No. PCT/JP2012/065349, mailed on Jul. 31, 2012.

*Primary Examiner* — Casey Bryant
(74) *Attorney, Agent, or Firm* — Keating & Bennett, LLP

(57) ABSTRACT

A particle detection device detects a biological particle. The particle detection device includes a collection unit that collects a particle to a collection substrate, a fluorescence detection unit that emits excitation light toward the particle collected on the collection substrate and receives fluorescence emitted from the particle, and a cleaning unit that removes the particle from the collection substrate at a refreshing position separated from a collection/heating position and a detection position. At the collection/heating position, the particle is collected onto the collection substrate by the collection unit. At the detection position, fluorescence is received by the fluorescence detection unit. With such a structure, the particle detection device in which the particle is highly accurately detected is provided.

6 Claims, 15 Drawing Sheets

(56) References Cited

U.S. PATENT DOCUMENTS

| | | |
|---|---|---|
| 2009/0103082 A1 | 4/2009 | Black et al. |
| 2011/0141454 A1 | 6/2011 | Henning et al. |
| 2012/0154348 A1 | 6/2012 | Okuno |

FOREIGN PATENT DOCUMENTS

| | | |
|---|---|---|
| JP | 4-26387 U | 3/1992 |
| JP | 7-83830 A | 3/1995 |
| JP | 2002-357532 A | 12/2002 |
| JP | 2004-347469 A | 12/2004 |
| JP | 2007-6709 A | 1/2007 |
| JP | 2007-528214 A | 10/2007 |
| JP | 2008-514911 A | 5/2008 |
| JP | 2010-054447 A | 3/2010 |
| JP | 2011-83214 A | 4/2011 |
| JP | 2011-97861 A | 5/2011 |
| WO | 2011/024672 A1 | 3/2011 |
| WO | 2011/104770 A1 | 9/2011 |

FLUORESCENCE MEASURING STEP
(AFTER HEATING)

REFRESHING STEP

CONCENTRATION N OF BIOLOGICAL PARTICLES (PARTICLES/m$^3$)

DETECTION POSITION | COLLECTION/HEATING POSITION | REFRESHING POSITION

PARTICLE DETECTION DEVICE

TECHNICAL FIELD

The present invention generally relates to a particle detection device and particularly relates to a particle detection device that detects biological particles.

BACKGROUND ART

As a related-art particle detection device, Japanese Unexamined Patent Application Publication No. 2002-357532, for example, discloses a measuring device for suspended particulate matter in order to simultaneously measure the densities of suspended particulate matter and pollen in the atmosphere (Patent Literature 1).

The measuring device disclosed in Patent Literature 1 includes a suspended particulate matter collection unit that collects suspended particulate matter in a sample gas onto filter paper, a suspended particulate matter detection unit that irradiates the suspended particulate matter on the filter paper with β-rays, measures the amount of β-ray transmission so as to detect the suspended particulate matter, and a pollen detection unit that irradiates the pollen contained in the suspended particulate matter with ultraviolet rays and measure the intensity of generated fluorescence so as to measure the amount of the pollen. The filter paper to which the suspended particulate matter has been collected is transported between the suspended particulate matter collection unit and a region where the suspended particulate matter detection unit and the pollen detection unit are disposed by using a filter paper transport mechanism, which includes rollers and motors combined to one another.

CITATION LIST

Patent Literature

PTL 1: Japanese Unexamined Patent Application Publication No. 2002-357532

SUMMARY OF INVENTION

Technical Problem

As disclosed in the above-described Patent Literature, a known detection device measures the number of particles by irradiating the particles in air with ultraviolet rays and receiving fluorescence emitted from the particles. In such a particle detection device, a collection member such as a substrate is used to collect particles. However, when such a collection member is replaced with a new collection member every time measurement is performed, there is a problem in that the cost of particle detection is increased.

As a measure to solve such a problem, the collection member may be repeatedly used by cleaning the collection member when particle detection is completed. However, there is a concern over adverse effects on accuracy, with which the particles are detected, in the case where the particles removed from the collection member by cleaning are collected again to the collection member or adhere to optical systems for irradiation of ultraviolet rays or receiving fluorescence.

Accordingly, an object of the present invention is to solve the above-described problem and is to provide a particle detection device in which particles are highly accurately detected.

Solution to Problem

A particle detection device according to the present invention detects a biological particle. The particle detection device includes a collection unit that collects a particle to a collection member, a fluorescence detection unit that emits excitation light toward the particle collected to the collection member and receives fluorescence emitted from the particle, and a cleaning unit that removes the particle from the collection member at a third position separated from a first position and a second position. The particle is collected by the collection unit to the collection member at the first position. The fluorescence is received by the fluorescence detection unit at the second position.

In the particle detection device structured as described above, the particle is removed from the collection member by the cleaning unit at the third position separated from the first position and the second position. This can reduce a situation, in which the particle having been removed from the collection member reaches the first position or the second position. Accordingly, the particle detection device in which the particle is highly accurately detected can be realized.

Preferably, the collection member is moved among the first position, the second position, and the third position. In a movement direction of the collection member, when seen from the first position, the third position is located on a side opposite to a side where the second position is located.

In the particle detection device structured as described above, the third position, where the particle is removed from the collection member, and the second position, where the fluorescence is received by the fluorescence detection unit, are separated from each other. Thus, the particle can be highly accurately detected.

Preferably, the first position, the second position, and the third position are arranged on a circumference. In the particle detection device structured as described above, the collection unit, the fluorescence detection unit, and the cleaning unit can be arranged in a compact space.

Preferably, the first position, the second position, and the third position are arranged on a line. In the particle detection device structured as described above, the third position, where the particle is removed from the collection member, and the second position, where the fluorescence is received by the fluorescence detection unit, are further separated from each other. Thus, the particle can be more highly accurately detected.

Preferably, the collection member is moved among the first position, the second position, and the third position. A moving distance of the collection member between the second position and the third position is greater than a moving distance of the collection member between the first position and the third position.

In the particle detection device structured as described above, the third position, where the particle is removed from the collection member, and the second position, where the fluorescence is received by the fluorescence detection unit, are separated from each other. Thus, the particle can be highly accurately detected.

Preferably, the particle detection device further includes a heating unit that heats the particle, which has been collected to the collection member, at the first position. More preferably, the heating unit is disposed in the collection member. In the particle detection device structured as described above, by heating the particle collected to the collection member, a biological particle can be highly accurately detected.

Advantageous Effects of Invention

As described above, according to the present invention, the particle detection device that highly accurately detects the particle can be provided.

DESCRIPTION OF EMBODIMENTS

Figure 1:
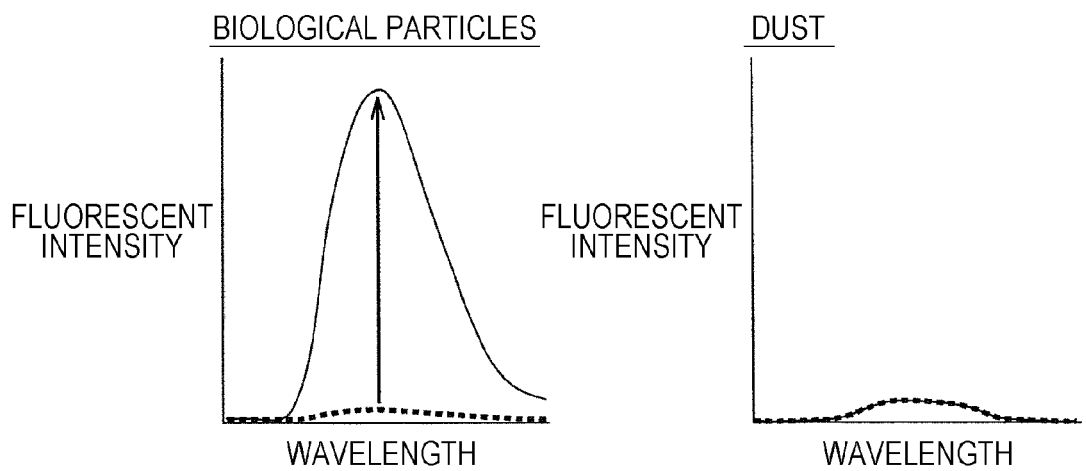
FIG. 1 includes graphs illustrating a change in fluorescent intensity of biological particles before and after heating and a change in fluorescent intensity of dust before and after heating.

Embodiments of the present invention will be described with reference to the drawings. In the drawings to be referred to in the description below, the same components or components equal to the same components are denoted by the same reference numerals.

(First Embodiment)
[Principle of Detection of Biological Particles]

A particle detection device according to the present embodiment detects biological particles such as pollen, microorganisms, and molds. The principle of detecting biological particles using the particle detection device according to the present embodiment is initially described.

FIG. 1 includes graphs illustrating a change in fluorescent intensity of biological particles before and after heating and a change in fluorescent intensity of dust before and after heating.

Airborne biological particles emit fluorescence when being irradiated with ultraviolet light or blue light. In air, however, other particles such as lint of chemical fiber (referred to as dust hereafter), which emit fluorescence similarly to biological particles, are also suspended. Thus, it is impossible to distinguish whether the light comes from biological particles or dust only by detecting fluorescence.

When, as illustrated in FIG. 1, biological particles and dust are heated and changes in the fluorescent intensities (amount of fluorescence) thereof are measured before and after heating, the fluorescent intensity emitted from the dust is not changed by heating and the fluorescent intensity emitted from the biological particles is increased by heating. The particle detection device according to the present embodiment measures the fluorescent intensity of a mixed particle of biological particles and dust before and after heating, and obtains the difference between the fluorescent intensity before and after the heating, thereby determining the number of the biological particles.

Figure 2:
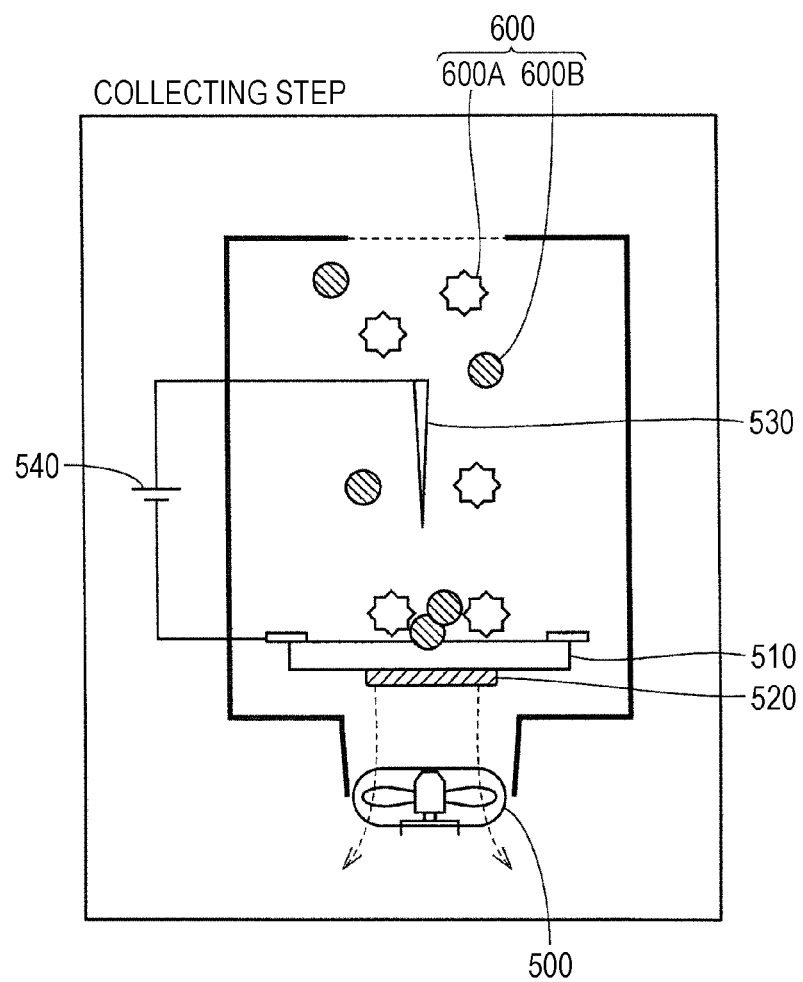
FIG. 2 illustrates a collecting step in biological particle detection.

FIGS. 2 to 6 illustrate steps of detecting biological particles. Referring to FIG. 2, particles are initially collected on a collection substrate 510 (collecting step).

In this step, the collection substrate 510 is disposed opposite an electrostatic stylus 530 and a potential difference is generated between the collection substrate 510 and the electrostatic stylus 530. When air is introduced toward the collection substrate 510 by driving a fan 500, airborne particles 600 around the electrostatic stylus 530 are charged. The charged particles 600 are attracted to a surface of the collection substrate 510 by electrostatic forces. The particles 600 collected on the collection substrate 510 includes biological particles 600A and dust 600B including, for example, lint of chemical fiber.

Figure 3:
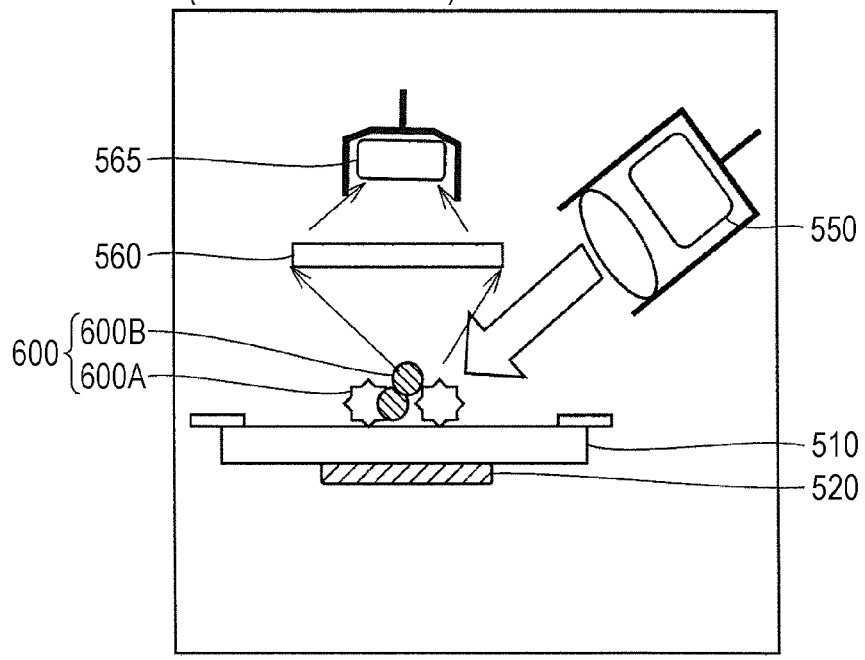
FIG. 3 illustrates a fluorescence measuring step (before heating) in the biological particle detection.

Next, referring to FIG. 3, the intensity of fluorescence emitted from the particles 600 before heating is measured (fluorescence measuring step (before heating)). In this step, the particles 600 collected on the collection substrate 510 is irradiated with excitation light emitted thereto from a light emitting element 550 such as a semiconductor laser, and fluorescence emitted from the particles 600 is received by a light receiving element 565 through a lens 560.

Figure 4:
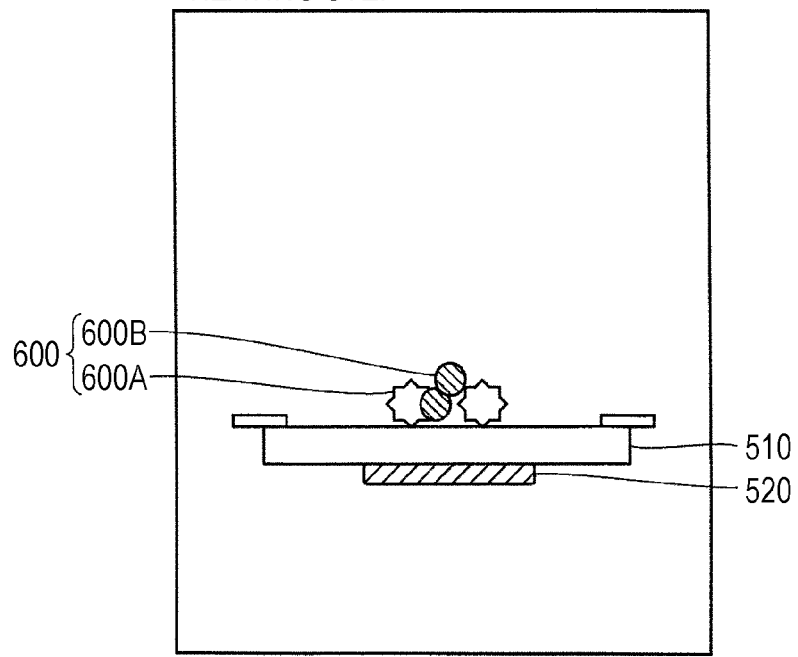
FIG. 4 illustrates a heating step in the biological particle detection.

Next, referring to FIG. 4, the particles 600 collected on the collection substrate 510 is heated by using a heater 520. After the particles 600 have been heated, the collection substrate 510 is cooled (heating step).

Figure 5:
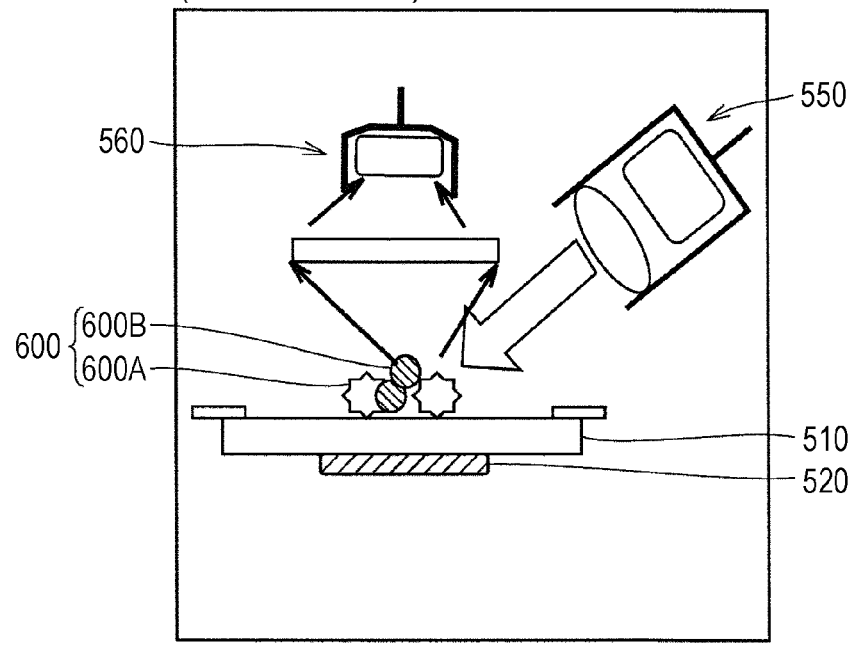
FIG. 5 illustrates a fluorescence measuring step (after heating) in the biological particle detection.

Referring to FIG. 5, next, the intensity of fluorescence emitted from the particles 600 after heating is measured (fluorescence measuring step (after heating)). As has been described, the intensity of fluorescence emitted from the dust 600B is not changed by heating, and the intensity of fluorescence emitted from the biological particles 600A is increased by heating. Thus, the fluorescent intensity measured in this step is greater than that measured in the fluorescence measuring step (before heating) illustrated in FIG. 3.

Figure 7:
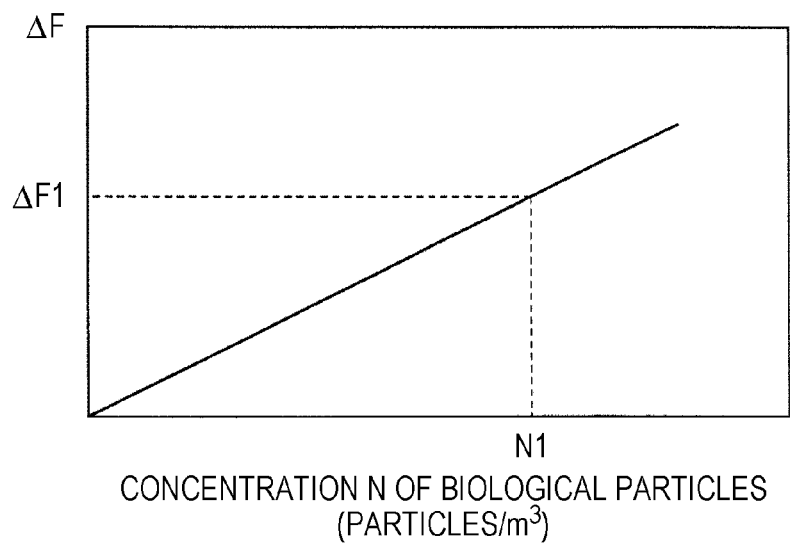
FIG. 7 is a graph illustrating the relationship between an increase ΔF in the fluorescent intensity after heating and the concentration of biological particles.

FIG. 7 is a graph illustrating the relationship between an increase ΔF in the fluorescent intensity after heating and the concentration of biological particles. Referring to FIG. 7, an increase ΔF1 in the fluorescent intensity is calculated from the difference in the fluorescent intensity before and after heating. The concentration N1 of biological particles corresponding to the calculated increase ΔF1 is found in accordance with a prepared relationship between the increase ΔF in the fluorescent intensity and the concentration N of biological particles. The correspondence relationship between the increase ΔF and the concentration N of biological particles is experimentally determined in advance.

Figure 6:
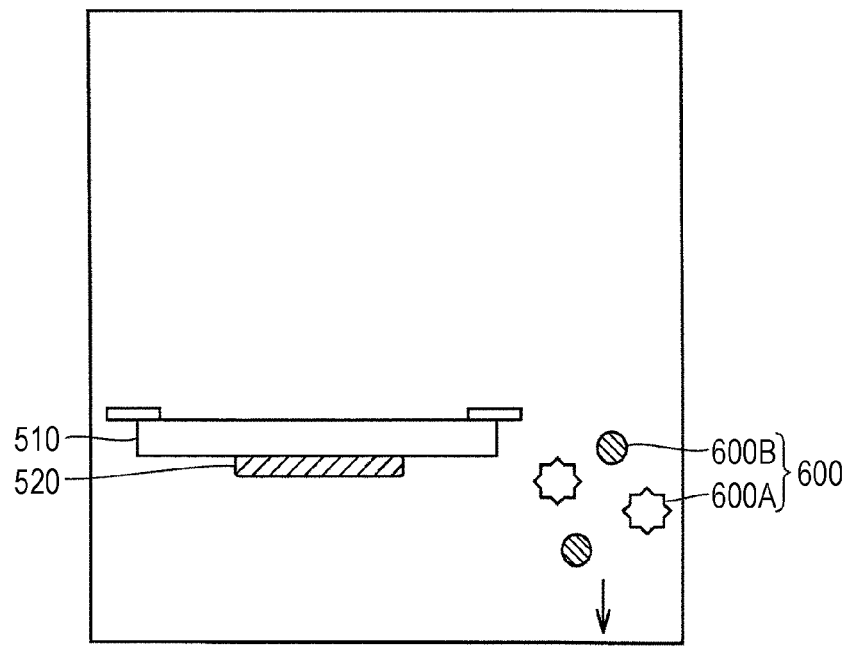
FIG. 6 illustrates a refreshing step in the biological particle detection.

Referring to FIG. 6, next, when detection of the biological particles of the particles 600 has been performed, the particles 600 are removed from the collection substrate 510 (refreshing step).

[General Structure of Particle Detection Device]

Figure 8:
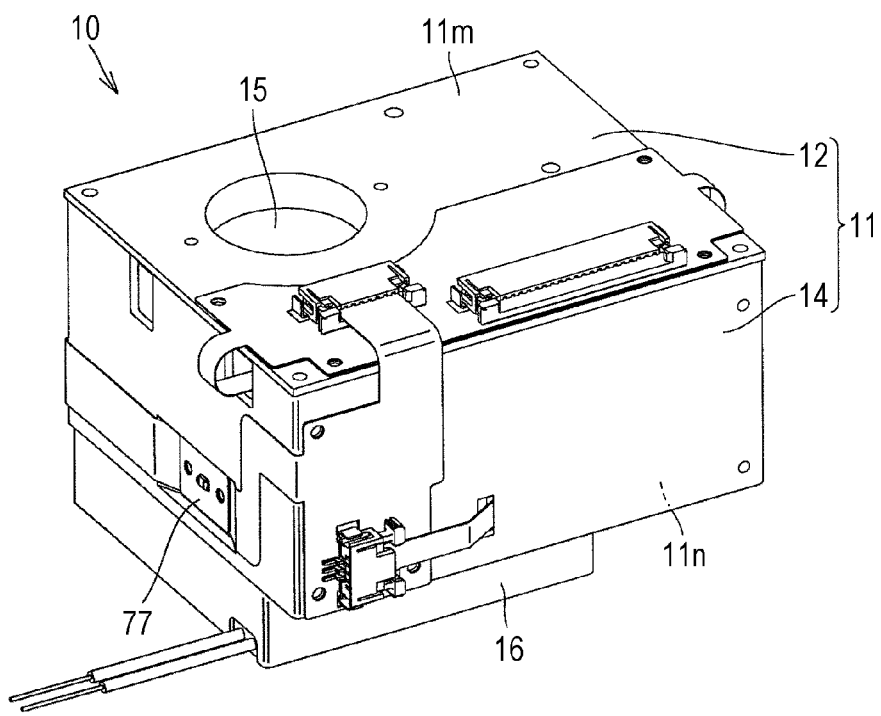
FIG. 8 is a perspective view illustrating the appearance of a particle detection device according to a first embodiment of the present invention.
Figure 9:
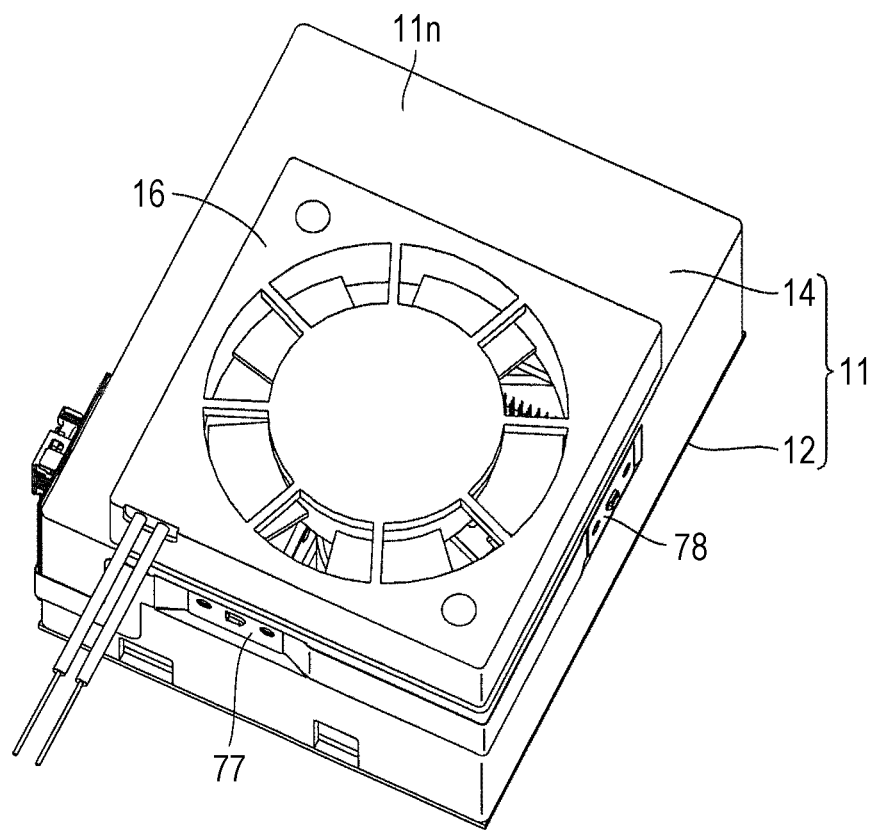
FIG. 9 is another perspective view illustrating the appearance of the particle detection device illustrated in FIG. 8.
Figure 10:
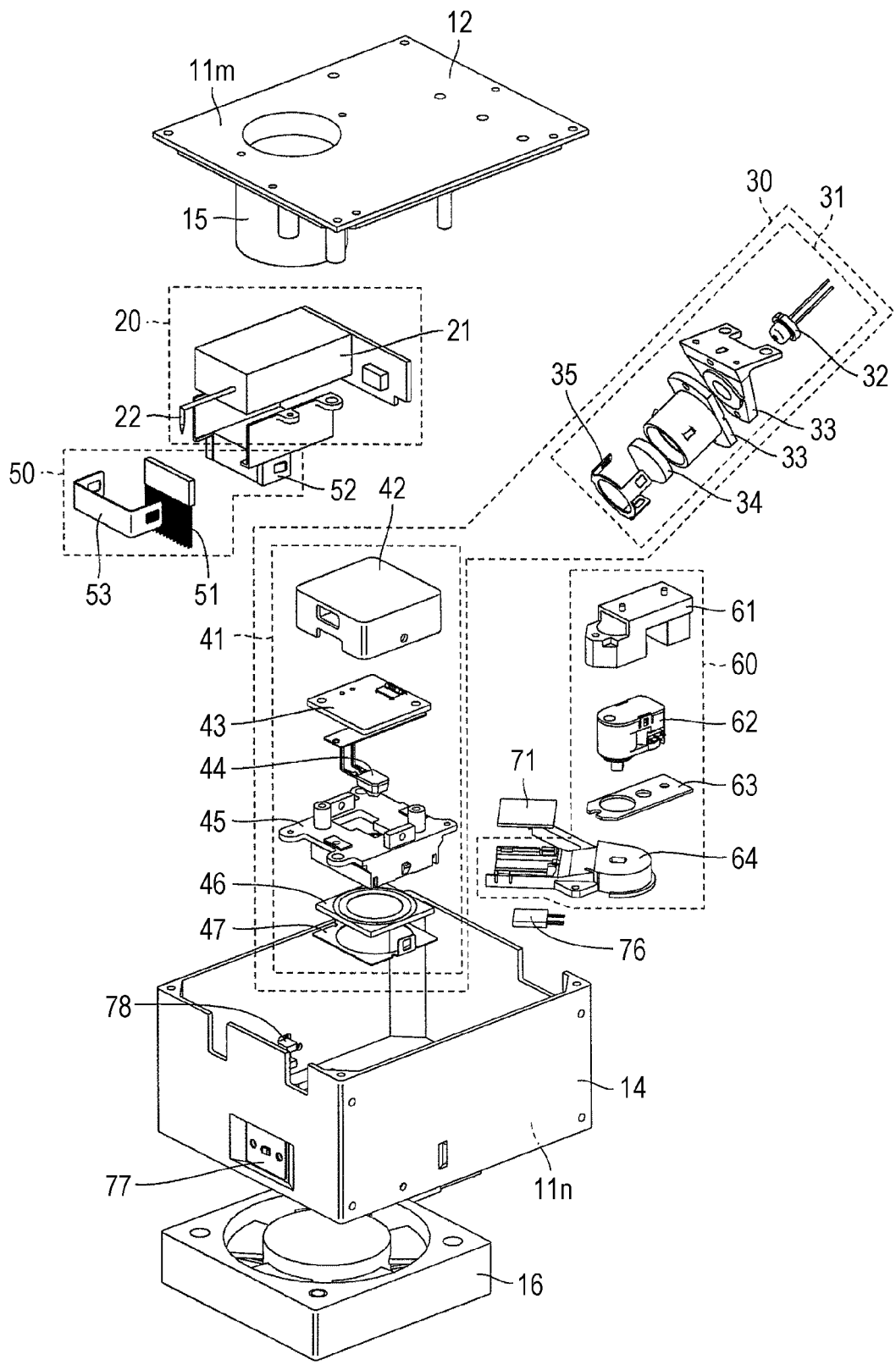
FIG. 10 is an exploded view of the particle detection device illustrated in FIG. 8.
Figure 11:
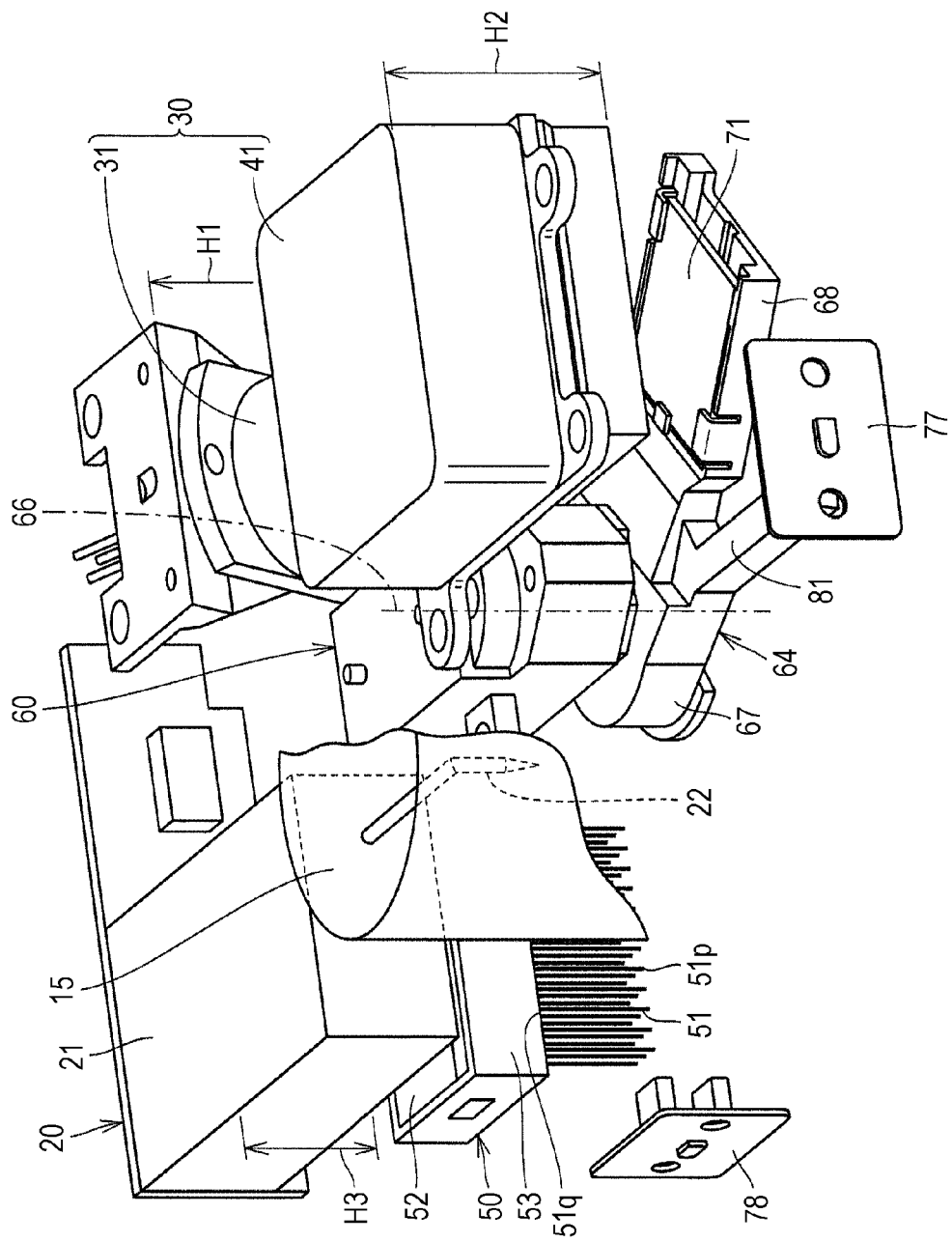
FIG. 11 is a perspective view illustrating an internal structure of the particle detection device illustrated in FIG. 8.

FIG. 8 is a perspective view illustrating the appearance of the particle detection device according to a first embodiment of the present invention. FIG. 9 is another perspective view illustrating the appearance of the particle detection device illustrated in FIG. 8. FIG. 10 is an exploded view of the particle detection device illustrated in FIG. 8. FIG. 11 is a perspective view illustrating an internal structure of the particle detection device illustrated in FIG. 8.

Referring to FIGS. 8 to 11, a particle detection device 10 according to the present embodiment includes a cabinet 11 serving as a housing, a fan 16, a collection unit 20, a fluorescence detection unit 30, and a cleaning unit 50.

The cabinet 11 has a substantially rectangular parallelepiped shape and houses the collection unit 20, the fluorescence detection unit 30, and the cleaning unit 50. In the present embodiment, the cabinet 11 includes an upper cabinet 12 serving as a first housing and a lower cabinet 14 serving as a second housing. The lower cabinet 14 has a box shape having an opening on one side. The upper cabinet 12 has a flat-plate shape that closes the opening of the lower cabinet 14. As an example, the dimensions of the cabinet 11 are 60 mm×50 mm (length and width of the upper cabinet 12)×30 mm (height).

The cabinet 11 has side surfaces 11m and 11n, which oppose each other. The side surface 11m is formed in the upper cabinet 12 and the side surface 11n is formed in the lower cabinet 14.

The cabinet 11 has a collection barrel 15 serving as a barrel-shaped member, which is integrally formed with the cabinet 11. The collection barrel 15 opens at the side surface 11m and extends so as to form a cylindrical shape from the side surface 11m toward the side surface 11n. The collection barrel 15 surrounds an electrostatic stylus 22, which will be described later. Air that includes particles is guided toward a collection substrate 71, which is positioned so as to oppose the electrostatic stylus 22, through the collection barrel 15.

Figure 12:
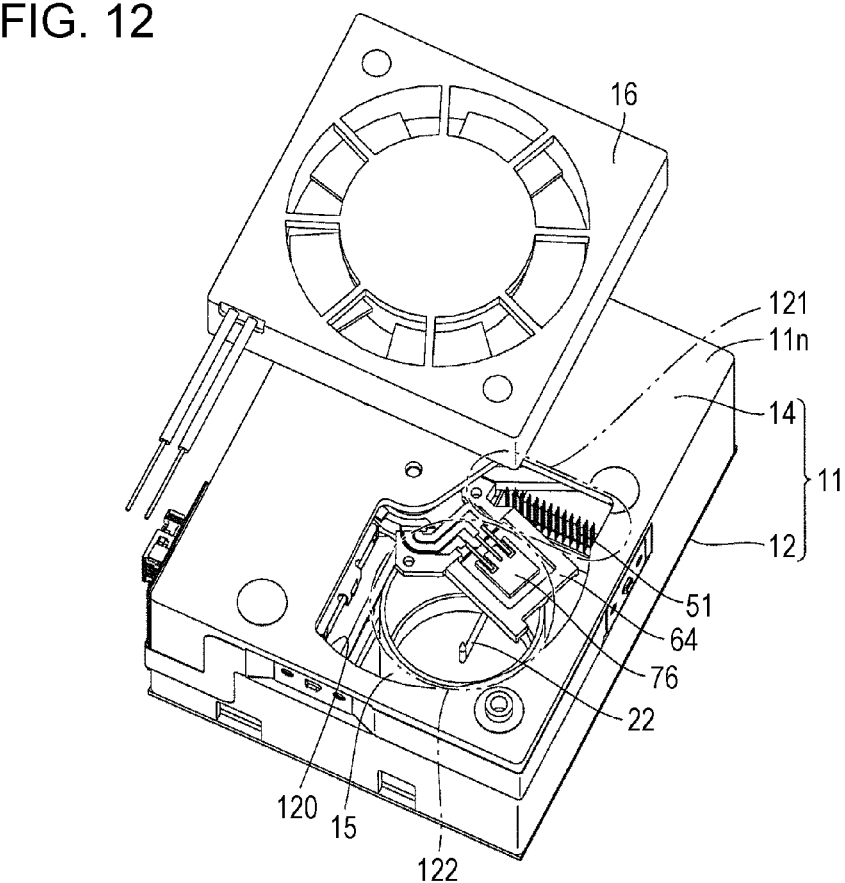
FIG. 12 is a perspective view illustrating the particle detection device illustrated in FIG. 9 with a fan detached.

FIG. 12 is a perspective view illustrating the particle detection device illustrated in FIG. 9 with the fan detached. Referring to FIGS. 9 and 12, the fan 16 is rotatable in the forward and reverse directions. When the fan 16 is rotated in the forward direction, air in the cabinet 11 is discharged to the outside of the cabinet 11 through the fan 16. When the fan 16 is rotated in the reverse direction, air is introduced from the outside of the cabinet 11 into the cabinet 11 through the fan 16.

The fan 16 is attached to the side surface 11n of the cabinet 11. An opening 120 is formed at a position of the cabinet 11 where the fan 16 is attached. The opening 120 is opened so as to include a region opposite the collection barrel 15 (region indicated by a two-dot chain line 122 in FIG. 12) and a region opposite a brush 51 (region indicated by a two-dot chain line 121 in FIG. 12). The brush 51 will be described later. In the opening 120, the region opposite the collection barrel 15 and the region opposite the brush 51 are continuous with each other.

With this structure, the fan 16 is used in the collecting step, for cooling in the heating step, and in the refreshing step. Thus, the size and the cost of the particle detection device 10 can be reduced.

Referring to FIGS. 8 to 11, the collection unit 20 performs the collecting step having been described with reference to FIG. 2, thereby collecting particles suspended in the air onto the collection substrate 71. The collection unit 20 includes a high-voltage power source 21 serving as a power unit and the electrostatic stylus 22 serving as a discharge electrode.

The collection substrate 71 serves as a collection member. Mixed particles of biological particles and dust such as lint of chemical fiber are collected onto the collection substrate 71. The collection substrate 71 is formed of a glass plate. An electrically conductive transparent film is formed on a surface of the glass plate that attracts the particles. The collection substrate 71 is not necessarily formed of a glass plate and may be formed of ceramic or metal. The film is not necessarily transparent. For example, a metal film may be formed on the surface of the collection substrate 71 formed of ceramic or the like. When the collection substrate 71 is formed of metal, the film is not necessarily formed on the surface of the collection substrate 71.

The high-voltage power source 21 is the power unit used to generate a potential difference between the collection substrate 71 and the electrostatic stylus 22.

The electrostatic stylus 22 extends from the high-voltage power source 21, penetrates through the collection barrel 15, and reaches the inside of the collection barrel 15. In the collecting step, the collection substrate 71 opposes the electrostatic stylus 22. In the present embodiment, the electrostatic stylus 22 is electrically connected to a positive electrode of the high-voltage power source 21. The film formed on the collection substrate 71 is electrically connected to a negative electrode of the high-voltage power source 21.

In the case where the electrostatic stylus 22 is electrically connected to the positive electrode of the high-voltage power source 21, the film formed on the collection substrate 71 may be connected to a ground potential. Alternatively, the electrostatic stylus 22 may be electrically connected to the negative electrode of the high-voltage power source 21 and the film formed on the collection substrate 71 may be electrically connected to the positive electrode of the high-voltage power source 21.

In the collecting step, when the fan 16 is rotated in the forward direction, air in the cabinet 11 is discharged and, at the same time, air outside the cabinet 11 is introduced toward the collection substrate 71 through the collection barrel 15. In so doing, by generating the potential difference between the electrostatic stylus 22 and the collection substrate 71 by using the high-voltage power source 21, airborne particles around the electrostatic stylus 22 are positively charged. The positively charged particles are moved to the collection substrate 71 by electrostatic forces and attracted to the electrically conductive film, thereby being collected onto the collection substrate 71.

As described above, in the particle detection device 10 according to the present embodiment, the particles are collected onto the collection substrate 71 by electrostatic collection that utilizes electrostatic forces. In this case, the particles can be reliably held on the collection substrate 71 during detection of the particles, and after the particles have been detected, the particles can be easily removed from the collection substrate 71.

By using the needle-shaped electrostatic stylus 22 as the discharge electrode, the charged particles can be attracted to a very narrow region of the surface of the collection substrate 71 opposite the electrostatic stylus 22, the region corresponding to a region irradiated with the light emitting element, which will be described later. Thus, in the fluorescence measuring step, microorganisms having been attracted can be efficiently detected.

The fluorescence detection unit 30 performs the fluorescence measuring steps (before and after heating) having been described with reference to FIGS. 3 and 5. The fluorescence detection unit 30 includes an excitation light source unit 31 and light receiving unit 41. The excitation light source unit 31 emits excitation light toward the particles collected on the collection substrate 71. The light receiving unit 41 receives fluorescence emitted from the particles as the particles are irradiated with the excitation light.

The excitation light source unit 31 includes a light emitting element 32 serving as a light source, an excitation unit frame 33, a condensing lens 34, and a lens pressing member 35. The light receiving unit 41 includes a noise shield 42, an amplification circuit 43, a light receiving element 44, a light receiving unit frame 45, a Fresnel lens 46, and a lens pressing member 47. The light emitting element 32 uses, for example, a semiconductor laser or an LED (light emitting diode) element. The wavelength of light emitted from the light emitting element 32 may be in an ultraviolet range or a visible range as long as the light can excite biological particles and cause the biological particles to emit fluorescent. The light receiving element 44 uses, for example, a photodiode or an image sensor.

The cleaning unit 50 performs the refreshing step having been described with reference to FIG. 6, thereby removing the particles from the collection substrate 71. The cleaning unit 50 includes the brush 51 as a cleaning device, a brush securing portion 52 as a base portion, and a brush pressing member 53. The cleaning unit 50 is secured to and supported by the high-voltage power source 21. The cleaning unit 50 remains stationary during the refreshing step.

The brush 51 is formed of a fiber assembly. The brush 51 is formed of an electrically conductive fiber assembly. The brush 51 is formed of, for example, a carbon fiber. It is preferable that the wire diameter of the fiber assembly of the brush 51 be from ϕ0.05 mm to ϕ0.2 mm.

The brush 51 has a free end 51p and a supported end 51q (see FIG. 11). The supported end 51q is disposed at an end portion opposite to the free end 51p. The supported end 51q is supported by the brush securing portion 52 and the brush pressing member 53. The brush 51 hangs down with the supported end 51q at the top and the free end 51p at the bottom. The brush 51 is secured and supported at a refreshing position 93, which will be described later. By moving the collection substrate 71 while the free end 51p of the brush 51 is in contact with the surface of the collection substrate 71, the particles are removed from the collection substrate 71.

Although a collection device that removes particles from the collection substrate 71 uses the brush 51 in the present embodiment, the present invention is not limited to this. For example, the collection device may be a flat plate-shaped wiper to be brought into contact with the surface of the collection substrate 71 or a nozzle, through which air is blown toward the surface of the collection substrate 71.

The particle detection device 10 further includes a heater 76 serving as a heating unit and a movement mechanism 60.

The heater 76 performs the heating step having been described with reference to FIG. 4, thereby heating the particles collected on the collection substrate 71.

The movement mechanism 60, to which the collection substrate 71 is attached, moves the collection substrate 71 in the collecting step, the fluorescence measuring steps (before and after heating), the refreshing step, and the heating step. The movement mechanism 60 includes a motor holder 61, a rotating motor 62, a motor pressing member 63, and a rotating base 64. The rotating motor 62 serves as a rotatable drive unit. The rotating base 64 serves as an arm unit.

Figure 13:
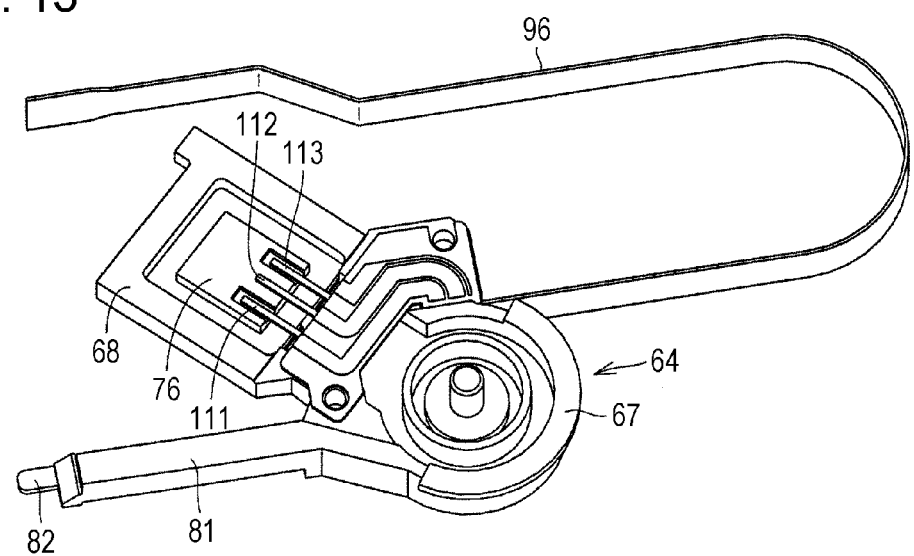
FIG. 13 is a perspective view illustrating a rotating base of a movement mechanism.
Figure 14:
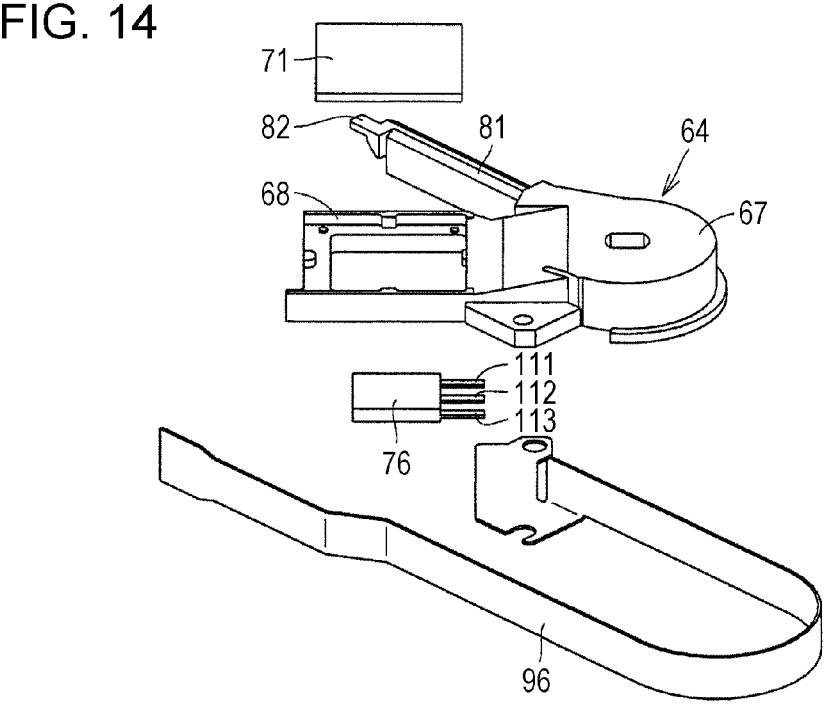
FIG. 14 is an exploded view of the rotating base illustrated in FIG. 13.

FIG. 13 is a perspective view illustrating the rotating base of the movement mechanism. FIG. 14 is an exploded view of the rotating base illustrated in FIG. 13. FIG. 13 illustrates the rotating base 64 when seen from a rear side (side surface 11n side of the cabinet 11). FIG. 14 illustrates the rotating base 64 when seen from a front side (side surface 11m side of the cabinet 11).

Referring to FIGS. 11, 13, and 14, an output shaft of the rotating motor 62 is connected to the rotating base 64. As the rotating motor 62 rotates, the rotating base 64 rotates (in the forward and reverse directions) about a rotational axis 66 illustrated by a phantom line in FIG. 11.

The rotating base 64 is formed of a resin material. The rotating base 64 has the following portions: a central portion 67, a substrate supporting portion 68, a brush cleaning arm 81 serving as a cleaning device initializing member, and a sensing target portion 82.

The central portion 67 is connected to the output shaft of the rotating motor 62. The central portion 67 is rotatably supported by the cabinet 11 about the rotational axis 66. The substrate supporting portion 68 extends from the central portion 67 in the radial direction of the rotational axis 66. The collection substrate 71 is attached to the tip of the substrate supporting portion 68. Part of the substrate supporting portion 68, the part being a part to which the collection substrate 71 is attached, has a frame shape. The details of the brush cleaning arm 81 and the sensing target portion 82 will be described later.

The heater 76 is bonded to the rear surface of the collection substrate 71. The heater 76 is moved together with the collection substrate 71 when the rotating base 64 is rotated. A plurality of wires 111, 112, and 113 are connected to the heater 76. The wires 111, 112, and 113 include a power supply line of the heater 76 and a signal line of a sensor disposed in the heater 76. The wires 111, 112, and 113 are led to the outside of the cabinet 11 through a flexible printed circuit 96.

Figure 15:
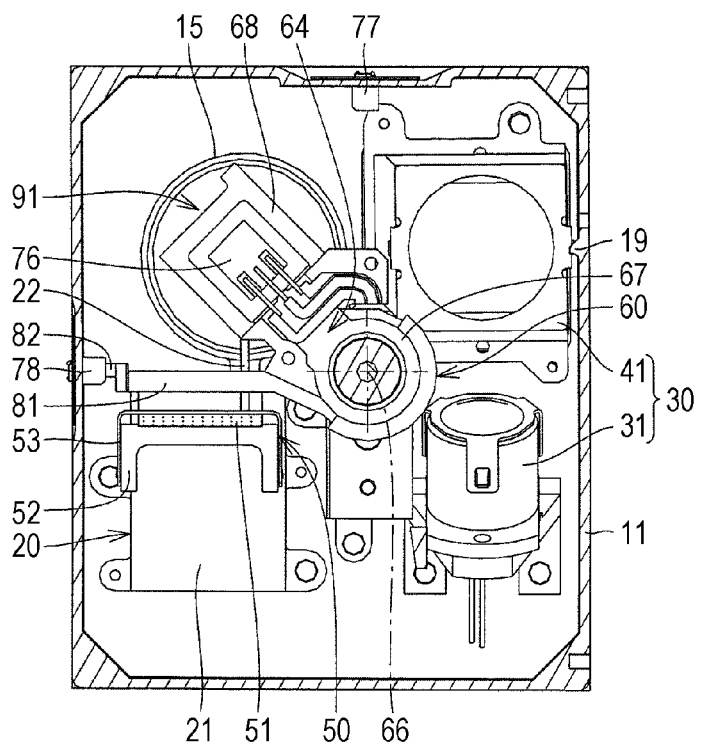
FIG. 15 is a sectional view of the particle detection device in the collecting step and the heating step.
Figure 16:
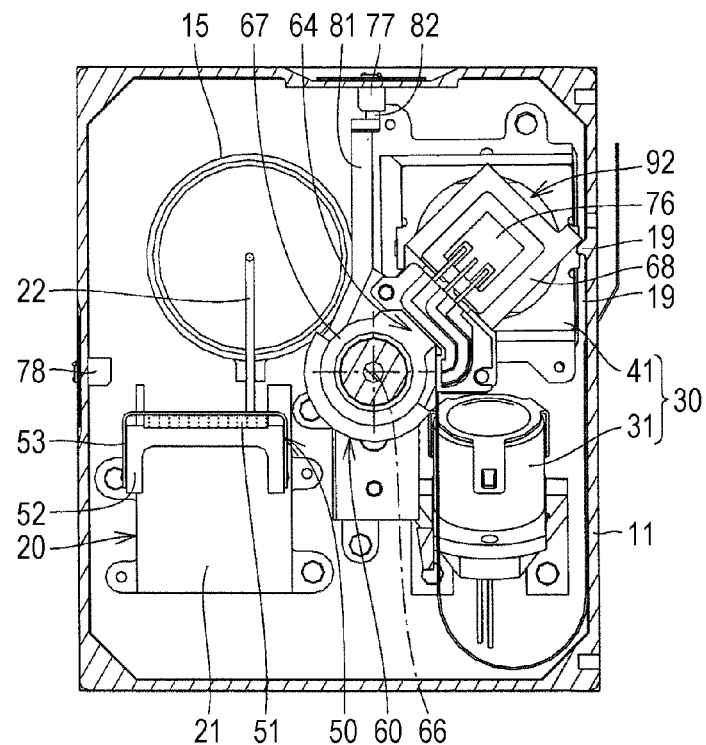
FIG. 16 is a sectional view of the particle detection device in the fluorescence measuring steps (before and after heating).

FIG. 15 is a sectional view of the particle detection device in the collecting step and the heating step. FIG. 16 is a sectional view of the particle detection device in the fluorescence measuring steps (before and after heating).

Figure 17:
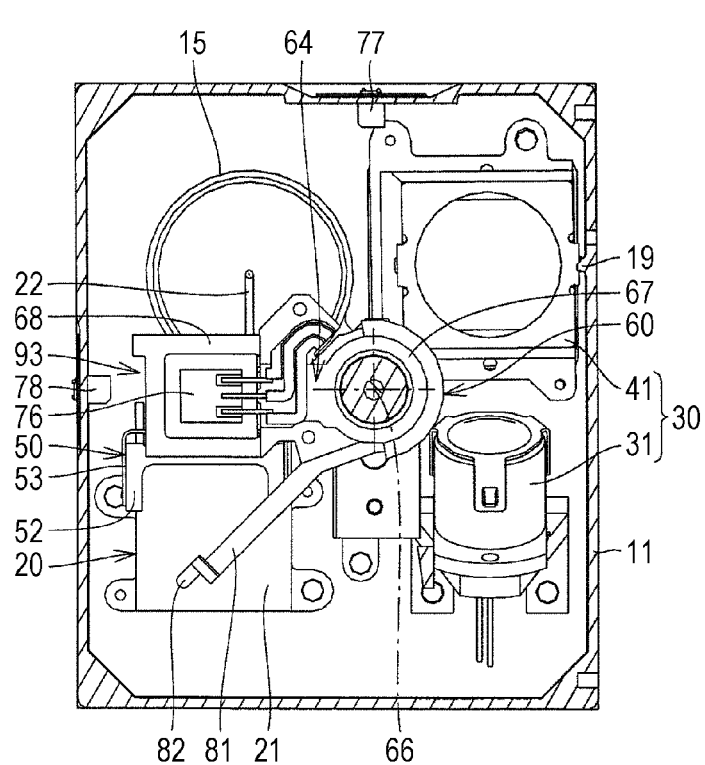
FIG. 17 is a sectional view of the particle detection device in the refreshing step.

FIG. 17 is a sectional view of the particle detection device in the refreshing step. FIGS. 15 to 17 are the sectional views of the particle detection device seen from the side surface 11n side of the cabinet 11.

Referring to FIGS. 15 to 17, in the particle detection device 10 according to the present embodiment, the collection substrate 71 is moved to a collection/heating position 91 illustrated in FIG. 15 as a first position in the collecting step and the heating step, moved to a detection position 92 illustrated in FIG. 16 as a second position in the fluorescence measuring steps (before and after heating), and moved to the refreshing position 93 illustrated in FIG. 17 as a third position in the refreshing step. The collection/heating position 91, the detection position 92, and the refreshing position 93 are separated from one another.

It is noted that the refreshing position 93 illustrated in FIG. 17 is a representative example of the refreshing position 93. In the actual refreshing step, the brush 51 is brought into contact with the surface of the collection substrate 71 while the collection substrate 71 is being moved, thereby removing the particles on the collection substrate 71. Thus, a movement range of the collection substrate 71 where the collection substrate 71 and the brush 51 are in contact with each other corresponds to the refreshing position 93.

The collection substrate 71 is held in a single plane while being moved among the collection/heating position 91, the detection position 92, and the refreshing position 93. The collection substrate 71 is held in the single plane perpendicular to the rotational axis 66 while being moved among the collection/heating position 91, the detection position 92, and the refreshing position 93.

That is, the particle detection device 10 according to the present embodiment includes the movement mechanism 60, which held the collection substrate 71 in the single plane while moving the collection substrate 71 among the collection/heating position 91, the detection position 92, and the refreshing position 93. Since the collection substrate 71 is moved in the single plane in the present embodiment, positioning accuracy of the collection substrate 71 can be improved at the collection/heating position 91, the detection position 92, and the refreshing position 93. Furthermore, since the collection substrate 71 is not moved in the axial direction of the rotational axis 66, the entire height of the particle detection device 10 can be reduced.

The collection/heating position 91, the detection position 92, and the refreshing position 93 are located on a circumference. The collection/heating position 91, the detection position 92, and the refreshing position 93 are arranged on the circumference about the rotational axis 66. In the movement direction of the collection substrate 71, the collection/heating position 91 is located between the detection position 92 and the refreshing position 93. In other words, in the movement direction of the collection substrate 71, the refreshing position 93 is located on a side of the collection/heating position 91 opposite to a side where the detection position 92 is located. In the movement direction of the collection substrate 71, the detection position 92, the collection/heating position 91, and the refreshing position 93 are arranged in this order.

The moving distance of the collection substrate 71 between the detection position 92 and the refreshing position 93 is greater than that between the collection/heating position 91 and the refreshing position 93. The movement range of the collection substrate 71 about the rotational axis 66 among the collection/heating position 91, the detection position 92, and the refreshing position 93 is equal to or smaller than 180°.

Figure 18:
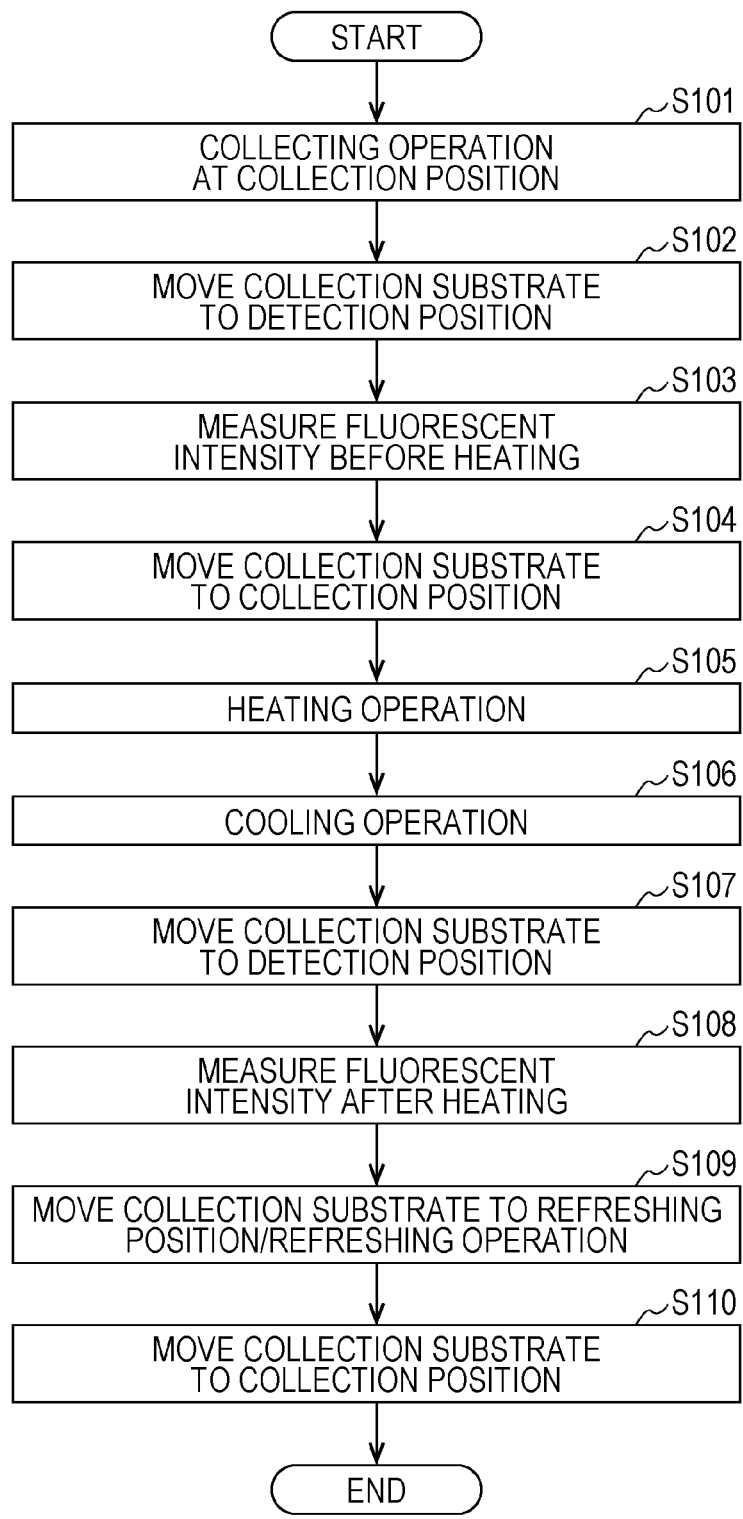
FIG. 18 is a flowchart illustrating a flow of operation of the particle detection device according to the first embodiment of the present invention.

Next, operation of the particle detection device 10 according to the present embodiment is described. FIG. 18 is a flowchart illustrating the flow of operation of the particle detection device according to the first embodiment of the present invention.

In the following description, a clockwise rotation about the rotational axis 66 in FIGS. 15 to 17 is referred to as a forward direction and a counterclockwise rotation about the rotational axis 66 in FIGS. 15 to 17 is referred to as a reverse direction.

Referring to FIGS. 15 and 18, the collection substrate 71 is initially positioned at the collection/heating position 91 so as to perform the collecting step (S101). In so doing, air is introduced into the cabinet 11 by rotating the fan 16 in the forward direction, and airborne particles are collected onto the surface of the collection substrate 71 by generating a potential difference between the electrostatic stylus 22 and the collection substrate 71 using the high-voltage power source 21.

Next, referring to FIGS. 16 and 18, the rotating base 64 is rotated in the forward direction by driving the rotating motor 62, thereby moving the collection substrate 71 from the collection/heating position 91 to the detection position 92 (S102). Next, the excitation light source unit 31 emits excitation light toward the particles collected on the collection substrate 71, and fluorescence emitted from the particles irradiated with the excitation light is received by the light receiving unit 41. By doing this, the fluorescent intensity of the particles collected on the collection substrate 71 before heating is measured (S103).

Next, referring to FIGS. 15 and 18, the rotating base 64 is rotated in the reverse direction by driving the rotating motor 62, thereby moving the collection substrate 71 from the detection position 92 to the collection/heating position 91 (S104). Next, by supplying power to the heater 76, the particles collected on the collection substrate 71 are heated (S105). Next, by stopping the power supply to the heater 76, the collection substrate 71 is cooled (S106). In so doing, by driving the fan 16 in the reverse direction, the air is introduced into the cabinet 11, thereby facilitating cooling of the collection substrate 71.

Next, referring to FIGS. 16 and 18, the rotating base 64 is rotated in the forward direction by driving the rotating motor 62, thereby moving the collection substrate 71 from the collection/heating position 91 to the detection position 92 (S107). Next, the excitation light source unit 31 emits the excitation light toward the particles collected on the collection substrate 71, and the fluorescence emitted from the particles irradiated with the excitation light is received by the light receiving unit 41. By doing this, the fluorescent intensity of the particles collected on the collection substrate 71 after heating is measured (S108).

Next, referring to FIGS. 17 and 18, the rotating base 64 is rotated in the reverse direction by driving the rotating motor 62, thereby moving the collection substrate 71 from the detection position 92 to the refreshing position 93. The rotating base 64 is rotated in the reverse direction and rotated in the forward direction at the refreshing position 93, thereby bringing the surface of the collection substrate 71 into contact with the brush 51. By doing this, the particles are removed from the collection substrate 71 (S109).

In the refreshing step, by driving the fan 16 in the forward direction, the particles removed from the collection substrate 71 and flying in the air are discharged to the outside of the cabinet 11 through the opening 120. In order to collect the particles discharged to the outside of the cabinet 11 through the opening 120, it is preferable that a filter be provided between the opening 120 and the fan 16.

In so doing, as the collection substrate 71 approaches from the collection/heating position 91 illustrated in FIG. 15 to the refreshing position 93 illustrated in FIG. 17, a region where the collection substrate 71 and the collection barrel 15 are superposed with each other is decreased. Accordingly, the area of an opening of the collection barrel 15 as an air inlet is increased. Thus, the particles can be efficiently collected at the outside the cabinet 11. In contrast, in the collecting step, the area of the opening of the collection barrel 15 is reduced by being blocked by the collection substrate 71. Thus, losses in air introduction can be reduced.

In the present embodiment, the refreshing step is performed by causing the cleaning unit 50 to remain stationary and moving the collection substrate 71. Accordingly, a separate movement mechanism for performing the refreshing step is not needed. Thus, the size and the cost of the particle detection device 10 can be reduced.

Referring to FIGS. 15 and 18, the rotating base 64 is rotated in the forward direction by driving the rotating motor 62, thereby moving the collection substrate 71 from the refreshing position 93 to the collection/heating position 91 (S110). By repeating the above-described steps S101 to S110, the biological particles are continuously detected.

The structure of the particle detection device according to the first embodiment of the present invention having been described is summarized as follows. That is, the particle detection device 10 according to the present embodiment detects biological particles. The particle detection device 10 includes the collection unit 20, the fluorescence detection unit 30, and the cleaning unit 50. The collection unit 20 collects particles onto the collection substrate 71 that serves as the collection member. The fluorescence detection unit 30 emits excitation light toward the particles collected on the collection substrate 71 and receives fluorescence emitted from the particles. The cleaning unit 50 removes the particles from the collection substrate 71 at the refreshing position 93 as the third position. The refreshing position 93 is separated from the collection/heating position 91 as the first position and the detection position 92 as the second position. At the collection/heating position 91, the particles are collected onto the collection substrate 71 by the collection unit 20. At the detection position 92, the fluorescence is received by the fluorescence detection unit 30.

In addition, the particle detection device 10 according to the present embodiment detects biological particles. The particle detection device 10 includes the collection unit 20, the fluorescence detection unit 30, the cleaning unit 50, and the movement mechanism 60. The collection unit 20 collects particles onto the collection substrate 71 that serves as the collection member. The fluorescence detection unit 30 emits excitation light toward the particles collected on the collection substrate 71 and receives fluorescence emitted from the particles. The cleaning unit 50 removes the particles from the collection substrate 71. The movement mechanism 60 moves the collection substrate 71 among the collection/heating position 91 as the first position, the detection position 92 as the second position, and the refreshing position 93 as the third position. At the collection/heating position 91, the particles are collected onto the collection substrate 71 by the collection unit 20. At the detection position 92, the fluorescence is received by the fluorescence detection unit 30. At the refreshing position 93, the cleaning unit 50 removes the particles from the collection substrate 71.

In addition, the particle detection device 10 according to the present embodiment detects biological particles. The particle detection device 10 includes the collection unit 20, the fluorescence detection unit 30, and the cleaning unit 50. The collection unit 20 collects particles onto the collection substrate 71 that serves as the collection member. The fluorescence detection unit 30 emits excitation light toward the particles collected on the collection substrate 71 and receives fluorescence emitted from the particles. The cleaning unit 50 removes the particles from the collection substrate 71. The collection substrate 71 is rotated in the forward and reverse directions, thereby being moved among the collection/heating position 91 as the first position, the detection position 92 as the second position, and the refreshing position 93 as the third position. At the collection/heating position 91, the particles are collected onto the collection substrate 71 by the collection unit 20. At the detection position 92, the fluorescence is received by the fluorescence detection unit 30. At the refreshing position 93, the cleaning unit 50 removes the particles from the collection substrate 71.

In the present embodiment, the cleaning unit 50 is provided for removing particles from the collection substrate 71. This allows the collection substrate 71 to be repeatedly used to detect biological particles. Thus, in comparison with the case where the collection substrate 71 is replaced every time a detection operation is performed, the cost required for particle detection can be reduced.

In the present embodiment, the refreshing step, in which particles are removed from the collection substrate 71, is performed at the refreshing position 93 separated from the collection/heating position 91 and the detection position 92. This can prevent the occurrence of the following situations: the particles having been removed from the collection substrate 71 are collected again to the collection substrate 71 in the next collecting step; and the particles having reached the detection position 92 from the collection substrate 71 adhere to optical systems such as the light emitting element 32 and the light receiving element 44. In particular, the collection/heating position 91 is located so as to separate the refreshing position 93 and the detection position 92 from each other in the present embodiment. This can effectively prevent the particles having been removed from the collection substrate 71 from reaching the detection position 92. For these reasons, biological particles can be highly accurately detected with the particle detection device 10 according to the present embodiment.

In the present embodiment, the collection/heating position 91, the detection position 92, and the refreshing position 93 are arranged on a circumference. Thus, the collection substrate 71 is moved among these positions by being rotated. With such a structure, the collection unit 20, the fluorescence detection unit 30, and the cleaning unit 50 can be arranged in a compact space, and accordingly, the size of the particle detection device 10 can be reduced. Furthermore, the collection substrate 71 is rotated in the forward and reverse directions so as to be moved to the collection/heating position 91, detection position 92, and the refreshing position 93 in the present embodiment. This prevents entanglement of a plurality of wires led through the flexible printed circuit 96 and wires for electrostatic collection.

The structure of the heater 76 as the heating unit is summarized as follows. That is, the particle detection device 10 according to the present embodiment includes the heater 76 as the heating unit that heats particles collected on the collection substrate 71. Biological particles are detected by the difference between the intensity of fluorescence emitted from the particles before heating and the intensity of fluorescence emitted from the particles after heating. The fluorescent intensity is measured by the fluorescence detection unit 30. When the particles are heated by the heater 76, the collection substrate 71 is moved to the collection/heating position 91 as the first position. The heater 76 is moved together with the collection substrate 71 by the movement mechanism 60. The collection substrate 71 having been heated by the heater 76 is cooled by air introduced into the cabinet 11 by the fan 16.

In the present embodiment, the heating step, in which particles collected on the collection substrate 71 is heated, is performed at the same position (collection/heating position 91) as that of the collecting step, in which the particles are collected onto the collection substrate 71. Thus, the size of the particle detection device 10 can be reduced. Furthermore, by disposing the heater 76 on the movement mechanism 60 and moving the heater 76 together with the collection substrate 71, the structure of the particle detection device 10 can be simplified.

[Arrangement of Components of Particle Detection Device]

Referring to FIG. 11 and FIGS. 15 to 17, in the present embodiment, the components of the collection unit 20, the fluorescence detection unit 30, and the cleaning unit 50 are arranged in the circumferential direction about the rotational axis 66.

The collection barrel 15 and the electrostatic stylus 22 oppose the collection/heating position 91. The high-voltage power source 21 and the cleaning unit 50 oppose the refreshing position 93. The light receiving unit 41 opposes the detection position 92.

The collection barrel 15 and the light receiving unit 41 are adjacent to each other in the circumferential direction about the rotational axis 66. The excitation light source unit 31 is adjacent to the light receiving unit 41 on a side opposite to a side where the collection barrel 15 is disposed in the circumferential direction about the rotational axis 66. That is, the light receiving unit 41 is disposed between the excitation light source unit 31 and the collection barrel 15 in the circumferential direction about the rotational axis 66. The excitation light source unit 31 is disposed on a side opposite to a side where the collection barrel 15 is disposed with the rotational axis 66 interposed therebetween.

The high-voltage power source 21 is adjacent to the collection barrel 15 on a side opposite to a side where the light receiving unit 41 is disposed in the circumferential direction about the rotational axis 66. That is, the collection barrel 15 is disposed between the high-voltage power source 21 and the light receiving unit 41 in the circumferential direction about the rotational axis 66. The high-voltage power source 21 is disposed on a side opposite to a side where the light receiving unit 41 is disposed with the rotational axis 66 interposed therebetween. The high-voltage power source 21 and the excitation light source unit 31 are adjacent to each other in the circumferential direction about the rotational axis 66.

When seen in the axial direction of the rotational axis 66, the collection barrel 15, the light receiving unit 41, and the high-voltage power source 21 are superposed with the movement range of the collection substrate 71 about the rotational axis 66. When seen in the axial direction of the rotational axis 66, the excitation light source unit 31 is shifted from the movement range of the collection substrate 71 about the rotational axis 66.

In the present embodiment, the excitation light source unit 31 is disposed opposite to the collection barrel 15 relative to the light receiving unit 41 in the movement direction of the collection substrate 71. With such a structure, an increase in the distance between the collection/heating position 91 and the detection position 92 due to arrangement of the excitation light source unit 31 is prevented.

When seen in the axial direction of the rotational axis 66, the cleaning unit 50 is superposed with the high-voltage power source 21. More specifically, the brush securing portion 52 of the cleaning unit 50 is attached to the high-voltage power source 21. As illustrated in FIG. 11, the excitation light source unit 31 and the light receiving unit 41 respectively have a height H1 (length in the axial direction of the rotational axis 66) and a height H2. The high-voltage power source 21 has a height H3. The height H3 is smaller than the height H1 and the height H2, and the height H1 is greater than the height H2 (H3<H2<H1).

In the present embodiment, the cleaning unit 50 is superposed with the high-voltage power source 21, which has the smallest height among the excitation light source unit 31, the light receiving unit 41, and the high-voltage power source 21. Thus, the components of the collection unit 20, the fluorescence detection unit 30, and the cleaning unit 50 are efficiently arranged in a limited space in the cabinet 11.

In the present embodiment, the cleaning unit 50 and the collection barrel 15 are adjacent to each other in the circumferential direction about the rotational axis 66. With such a structure, the fan 16 can be used in the collecting step, for cooling in the heating step, and in the refreshing step.

Figure 19:
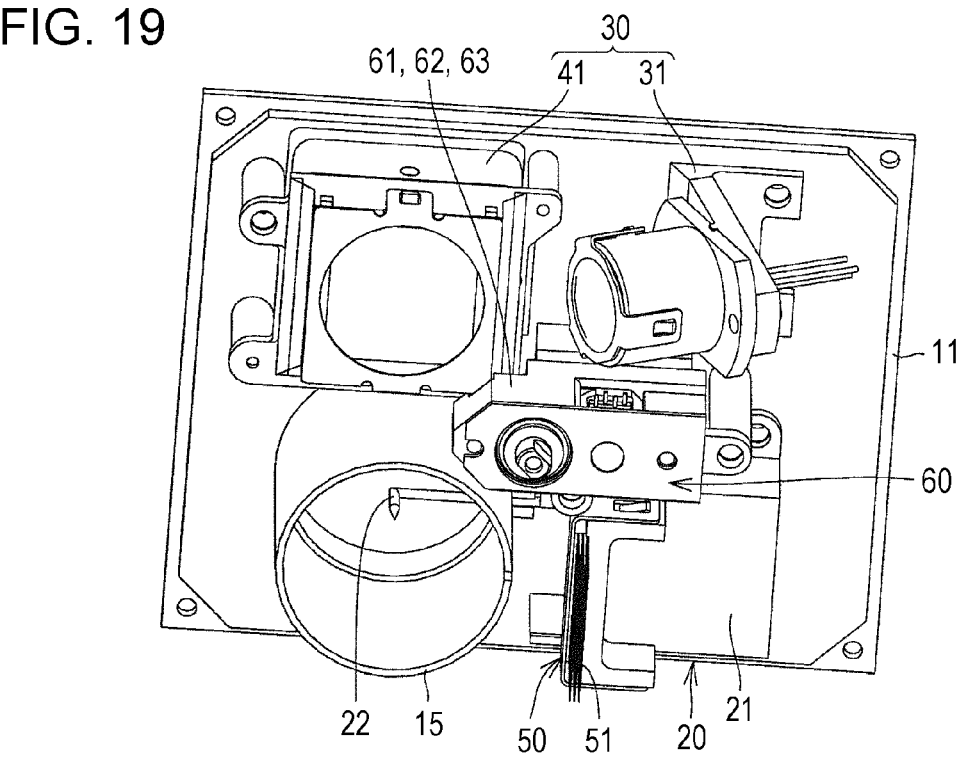
FIG. 19 is a perspective view illustrating an internal structure of the particle detection device.

FIG. 19 is a perspective view illustrating an internal structure of the particle detection device. Referring to FIG. 19, the collection barrel 15 and the movement mechanism 60 are provided so as to separate the light receiving unit 41 and the excitation light source unit 31 from the cleaning unit 50.

Such a structure can effectively reduce a situation in which particles having been removed from the collection substrate 71 at the refreshing position 93 reach the detection position 92. Furthermore, there is no need of providing partitions in the cabinet 11 in order to prevent the particles from reaching from the refreshing position 93 to the detection position 92, and accordingly, the collection/heating position 91, the detection position 92, and the refreshing position 93 can be located in a single space in the cabinet 11. Thus, the size of the particle detection device 10 can be reduced.

[Brush Cleaning Structure]

In the refreshing step, as the particles are removed from the collection substrate 71 by the cleaning unit 50, the particles adhere to the brush 51 in contact with the surface of the collection substrate 71. The particle detection device 10 according to the present embodiment includes the brush cleaning arm 81 serving as the cleaning device initializing member. The particles that adhere to the brush 51 are removed by the brush cleaning arm 81.

Referring to FIGS. 13 and 14, the brush cleaning arm 81 is integrated with the rotating base 64. The brush cleaning arm 81 is moved together with the collection substrate 71 when the rotating base 64 is rotated. The brush cleaning arm 81 extends in the radial direction of the rotational axis 66 from the central portion 67 of the rotating base 64. The particles adhering to the brush 51 are removed by rotating the brush cleaning arm 81 while the brush cleaning arm 81 is in contact with the free end 51p of the brush 51.

The brush cleaning arm 81 is disposed at a position shifted from the substrate supporting portion 68 in the circumferential direction about the rotational axis 66. As illustrated in FIG. 16, when the collection substrate 71 has been moved to the detection position 92, the brush cleaning arm 81 is positioned between the collection substrate 71 and the brush 51.

Figure 20:
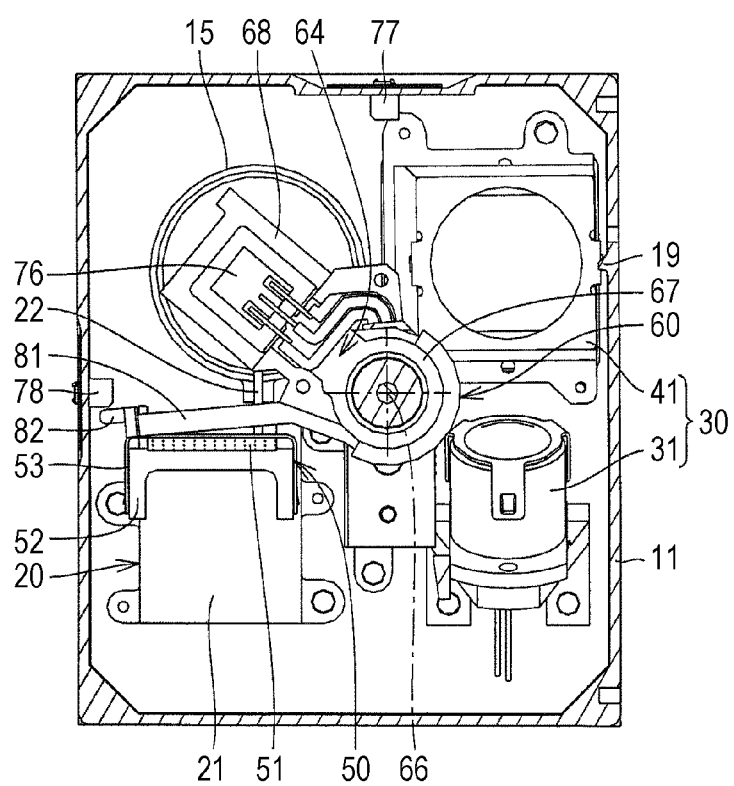
FIG. 20 is a sectional view illustrating movements of a collection substrate and a brush cleaning arm in the refreshing step.
Figure 21:
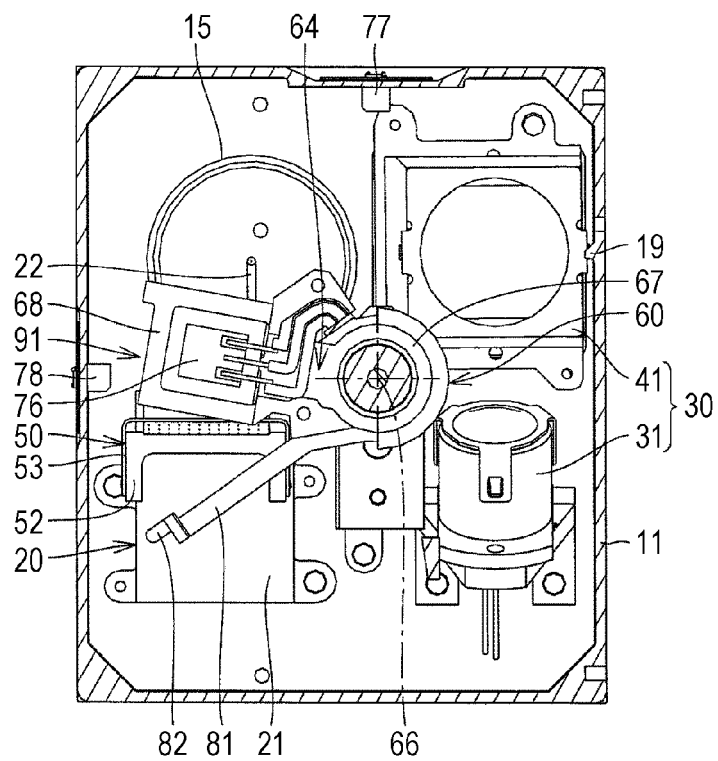
FIG. 21 is another sectional view illustrating the movements of the collection substrate and the brush cleaning arm in the refreshing step.
Figure 22:
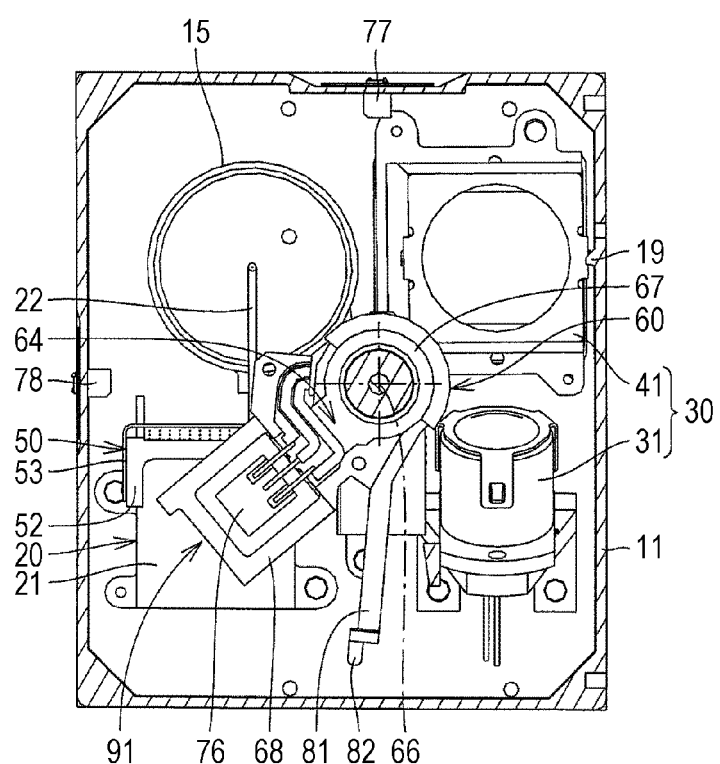
FIG. 22 is yet another sectional view illustrating the movements of the collection substrate and the brush cleaning arm in the refreshing step.

FIGS. 20 to 22 are sectional views illustrating the movements of the collection substrate and the brush cleaning arm in the refreshing step. In FIG. 22, an end of the movement range of the collection substrate 71 in the refreshing step is illustrated.

Referring to FIGS. 20 to 22, after the fluorescent intensity of the particles after heating have been measured, the rotating base 64 is rotated in the reverse direction, thereby moving the collection substrate 71 from the detection position 92 to the refreshing position 93.

In so doing, the particles adhering to the brush 51 are removed initially by moving the brush cleaning arm 81 in the reverse direction while the brush cleaning arm 81 is in contact with the free end 51p of the brush 51. At the same time, the particles having been removed from the brush 51 are collected from the refreshing position 93 to the outside of the cabinet 11 by driving the fan 16 in the forward direction. The rotating base 64 is further rotated in the reverse direction so as to cause the surface of the collection substrate 71 to be brought into contact with the brush 51, thereby removing the particles from the collection substrate 71. When the collection substrate 71 has been moved to the end of the movement range illustrated in FIG. 22, the rotating base 64 is rotated in the forward direction so as to cause the surface of the collection substrate 71 to be brought into contact with the brush 51 again, thereby removing the particles from the collection substrate 71.

In the present embodiment, when the collection substrate 71 has been moved to the detection position 92, the brush cleaning arm 81 is positioned between the collection substrate 71 and the brush 51. Thus, the brush cleaning arm 81 is brought into contact with the brush 51 before the collection substrate 71 is brought into contact with the brush 51. Accordingly, the collection substrate 71 can be cleaned by the brush 51, which has been refreshed with the brush cleaning arm 81. Thus, the particles can be efficiently removed from the collection substrate 71.

Furthermore, the brush cleaning arm 81 is integrated with the rotating base 64, to which the collection substrate 71 is attached. With such a structure, a separate movement mechanism for moving the brush cleaning arm 81 is not required. Thus, the size and the cost of the particle detection device 10 can be reduced.

Furthermore, a particle capturing portion having adhesiveness may be provided in the cabinet 11. The particle capturing portion is formed of, for example, an adhesive sheet. Preferably, the particle capturing portion is provided at the refreshing position 93 or a position between the refreshing position 93 and the collection/heating position 91. With such a structure, in addition to collection of the particles by driving the fan 16, the particles removed from the collection substrate 71 or the brush 51 can be collected by the particle capturing portion.

Figure 23:
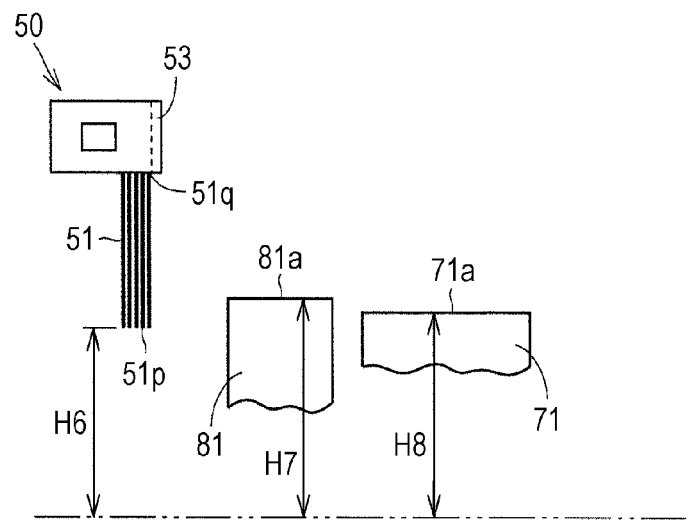
FIG. 23 illustrates height relationships among a brush, the brush cleaning arm, and the collection substrate.

FIG. 23 illustrates height relationships among the brush, the brush cleaning arm, and the collection substrate. Referring to FIG. 23, the brush cleaning arm 81 and the collection substrate 71 respectively have top surfaces 81a and 71a to be in contact with the free end 51p of the brush 51. When, with reference to a given position, the height of the free end 51p of the brush 51 is defined as H6, the height of the top surface 81a of the brush cleaning arm 81 is defined as H7, and the height of the top surface 71a of the collection substrate 71 is defined as H8, it is preferable that the following relationship be satisfied: H6 <H8<H7.

[Detailed Structure of Particle Detection Device]

The particle detection device 10 according to the present embodiment includes a position sensor 77, a position sensor 78, and the sensing target portion 82. The position sensors 77 and 78 serve as position detection units that detect the position of the collection substrate 71.

Referring to FIGS. 11, 15, and 16, the position sensors 77 and 78 detect the position of the collection substrate 71 by detecting that the sensing target portion 82 comes to the proximity of the position sensor 77 or 78. The position sensors 77 and 78 are attached to inner walls of the cabinet 11. The position sensors 77 and 78 are provided in a single plane perpendicular to the rotational axis 66. When seen in the axial direction of the rotational axis 66, the position sensor 77 is disposed between the collection/heating position 91 and the detection position 92, and the position sensor 78 is disposed between the collection/heating position 91 and the refreshing position 93.

Referring to FIG. 13, the sensing target portion 82 is integrated with the rotating base 64. The sensing target portion 82 is moved together with the collection substrate 71 when the rotating base 64 is rotated. The sensing target portion 82 is provided at the tip of the brush cleaning arm 81 that extends from the central portion 67 of the rotating base 64 in the radial direction of the rotational axis 66.

Referring to FIGS. 11, 15, and 16, a controller (not shown) detects that, when the position sensor 78 detects that the sensing target portion 82 comes to the proximity of the position sensor 78, the collection substrate 71 is positioned at the collection/heating position 91. At this time, the controller issues a command to the collection unit 20 and the fan 16 so as to start collection of particles onto the collection substrate 71. Furthermore, the controller detects that, when the position sensor 77 detects that the sensing target portion 82 comes to the proximity of the position sensor 77, the collection substrate 71 is positioned at the detection position 92. At this time, the controller issues an instruction to the fluorescence detection unit 30 so as to start detection of biological particles.

With the detection of the position of the collection substrate 71 by using the position sensors 77 and 78, positional accuracy of the collection substrate 71 in the collecting step and the detecting step can be improved, and accordingly, repeatability of the detection of the biological particles can be improved.

Referring to FIG. 16, the particle detection device 10 according to the present embodiment includes a projecting portion 19, which is disposed at the end of the movement range of the movement mechanism 60 and serves as a regulating member that regulates the movement of the movement mechanism 60. The projecting portion 19 projects from an inner wall of the cabinet 11. The projecting portion 19 is adjacent to the detection position 92. When the collection substrate 71 has been moved to the detection position 92, the rotating base 64 is brought into contact with the projecting portion 19. Thus, a further movement of the rotating base 64 is regulated.

The particle detection device 10 according to the present embodiment may be used as a single device that detects biological particles, or may be incorporated in a home appliance such as an air cleaner, an air conditioner, a humidifier, a dehumidifier, a cleaner, a refrigerator, or a television set.

(Second Embodiment)

Figure 24:
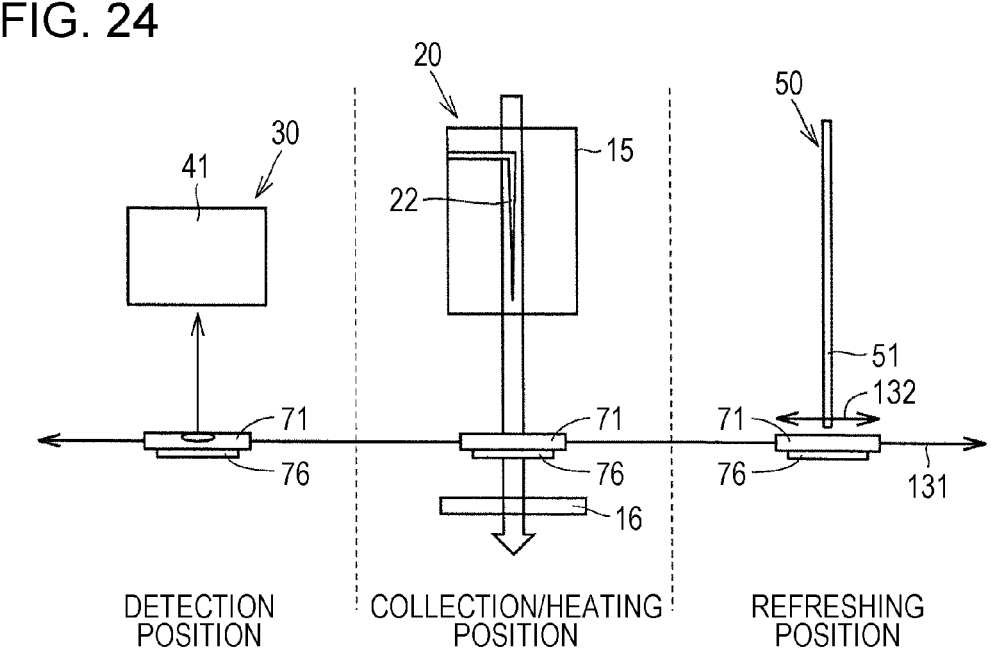
FIG. 24 is a plan view illustrating a particle detection device according to a second embodiment of the present invention.
Figure 25:
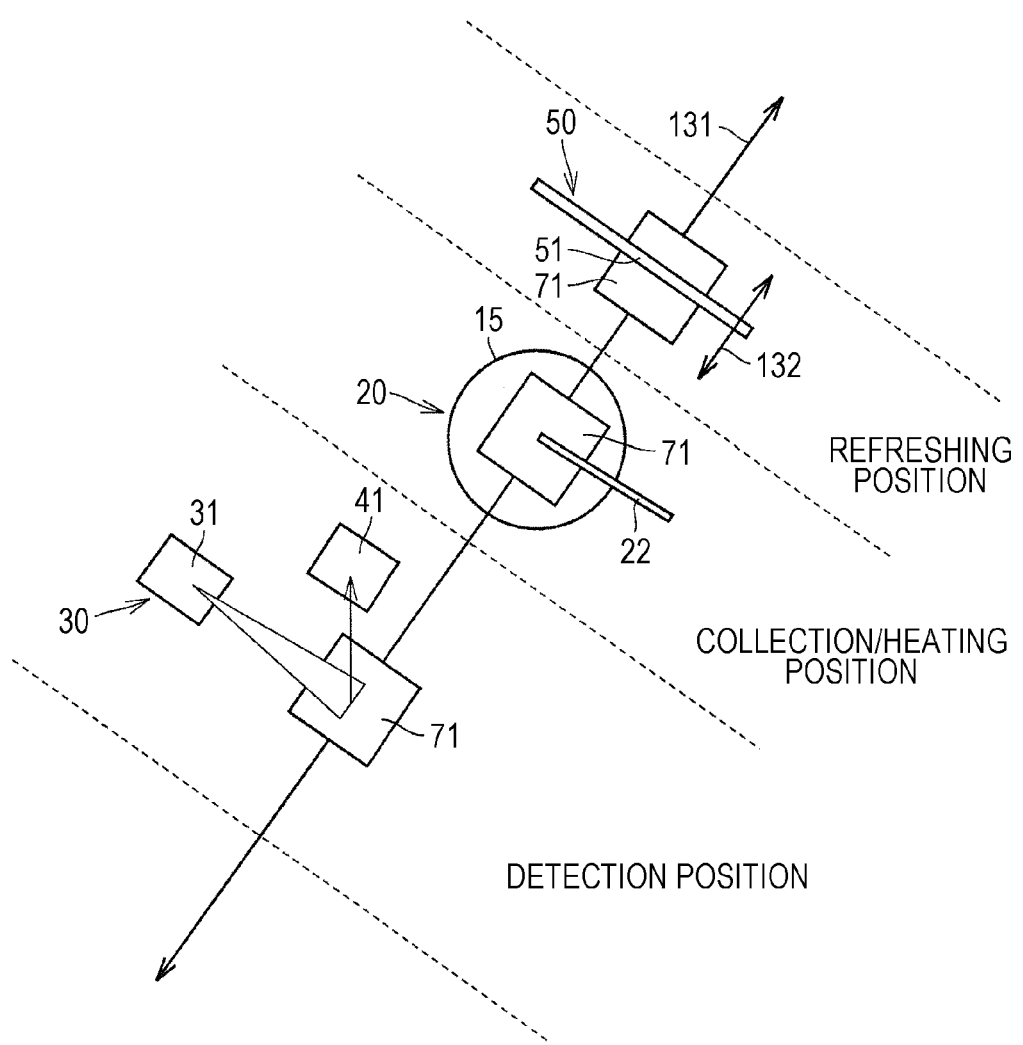
FIG. 25 is a side view of the particle detection device illustrated in FIG. 24.

FIG. 24 is a plan view illustrating a particle detection device according to a second embodiment of the present invention. FIG. 25 is a side view of the particle detection device illustrated in FIG. 24. The particle detection device according to the present embodiment basically has similar structures compared to those of the particle detection device 10 according to the first embodiment. Duplicate structures are not repeatedly described in the following description.

Referring to FIGS. 24 and 25, in the particle detection device according to the present embodiment, the collection/heating position 91, the detection position 92, and the refreshing position 93 are arranged on a line. The collection substrate 71 attached to a movement mechanism (not shown) is moved among the collection/heating position 91, the detection position 92, and the refreshing position 93 while being reciprocated in a direction indicated by a double-headed arrow 131. By the reciprocation of the collection substrate 71 in a double-headed arrow 132 direction at the refreshing position 93, particles collected on the collection substrate 71 are removed.

In the movement direction of the collection substrate 71, the collection/heating position 91 is located between the detection position 92 and the refreshing position 93. In other words, in the movement direction of the collection substrate 71, the refreshing position 93 is located on a side of the collection/heating position 91 opposite to a side where the detection position 92 is located. In the movement direction of the collection substrate 71, the detection position 92, the collection/heating position 91, and the refreshing position 93 are arranged in this order.

In the present embodiment, the collection/heating position 91, the detection position 92, and the refreshing position 93 are arranged on a line. Thus, compared to the first embodiment in which these positions are arranged on a circumference, the distance between the detection position 92 and the refreshing position 93 can be increased. This can effectively prevent a situation in which particles having been removed from the collection substrate 71 at the refreshing position 93 from reaching the detection position 92.

The collection unit 20, the fluorescence detection unit 30, and the cleaning unit 50 are configured such that the detection position 92 is located between the collection/heating position 91 and the refreshing position 93 in the movement direction of the collection substrate 71.

Although the present invention has been described and illustrated in detail, it is clearly understood that the same is by way of illustration and example only and is not to be taken by way of limitation, the scope of the present invention being interpreted by the terms of the appended claims.

Industrial Applicability

The present invention is mainly used as a device that detects biological particles such as pollen, microorganisms, and molds.

Reference Signs List 10 particle detection device, 11 cabinet, 11m, 11n side surface, 12 upper cabinet, 14 lower cabinet, 15 collection barrel, 16 fan, 19 projecting portion, 20 collection unit, 21 high-voltage power source, 22 electrostatic stylus, 30 fluorescence detection unit, 31 excitation light source unit, 32 light emitting element, 33 excitation unit frame, 34 condensing lens, 41 light receiving unit, 42 noise shield, 43 amplification circuit, light receiving element, 45 light receiving unit frame, Fresnel lens, 50 cleaning unit, 51 brush, 51p free end, 51q supported end, 52 brush securing portion, 53 brush pressing member, 60 movement mechanism, 61 motor holder, 62 rotating motor, 64 rotating base, 66 rotational axis, 67 central portion, 68 substrate supporting portion, 71 collection substrate, 71a, 81a top surface, 76 heater, 77,78 position sensor, 81 brush cleaning arm, 82 sensing target portion, 91 collection/heating position, 92 detection position, 93 refreshing position, 96 flexible printed circuit, 111,112,113 wire, and 120 opening.

The invention claimed is:

1. A particle detection device that detects a biological particle, the particle detection device comprising:
a collector that is configured to collect a particle and to provide the collected particle to a collection member, the collection member having a flat planar shape;
a fluorescence detector that is configured to emit excitation light toward the particle provided to the collection member and to receive fluorescence emitted from the particle;
a cleaner that is configured to remove the particle from the collection member at a third position, the particle being collected by the collector and provided to the collection member at a first position, the fluorescence being received by the fluorescence detector at a second position; and
a movement mechanism that is configured to hold the collection member in a single plane while moving the collection member among the first position, the second position, and the third position; wherein
in a movement direction of the collection member, when seen from the first position, the third position is located on a side opposite to a side where the second position is located,
the collector includes a collection barrel that is a barrel-shaped member, the collector being configured to guide air including the particle toward the collection member,
the fluorescence detector includes an excitation light source that is configured to emit excitation light toward the particle and a light receiver that is configured to receive fluorescence emitted from the particle,
the collection barrel is provided immediately above the collection member at the first position, the light receiver and the excitation light source are provided at the second position, and the cleaner is provided at the third position, the third position being separated from the first position and the second position, and
the movement mechanism is configured to rise up from the single plane in which the collection member is moved to define a partition between the third position and the second position together with the collection barrel.

2. The particle detection device according to claim 1, wherein the first position, the second position, and the third position are arranged about a circumference of the particle detection device.

3. The particle detection device according to claim 1, wherein the first position, the second position, and the third position are arranged on a straight or substantially straight line within the particle detection device.

4. The particle detection device according to claim 1, wherein a moving distance of the collection member between the second position and the third position is greater than a moving distance of the collection member between the first position and the third position.

5. The particle detection device according to claim 1, further comprising:
a heater that is configured to heat the particle at the first position after the particle has been provided to the collection member.

6. The particle detection device according to claim 5, wherein the heater is disposed in the collection member.

* * * * *